United States Patent
Yamamoto

(10) Patent No.: US 6,514,218 B2
(45) Date of Patent: Feb. 4, 2003

(54) POSTURE DETECTING DEVICE AND BREATHING FUNCTION MEASURING DEVICE

(75) Inventor: Shinji Yamamoto, Toyokawa (JP)

(73) Assignee: Minolta Co., Ltd., Osaka (JP)

( * ) Notice: Subject to any disclaimer, the term of this patent is extended or adjusted under 35 U.S.C. 154(b) by 35 days.

(21) Appl. No.: 09/752,870

(22) Filed: Dec. 28, 2000

(65) Prior Publication Data

US 2001/0007923 A1 Jul. 12, 2001

(30) Foreign Application Priority Data

Jan. 7, 2000 (JP) .......................................... 2000-005882

(51) Int. Cl.[7] ................................................. A61B 5/00
(52) U.S. Cl. ...................... 600/587; 606/130; 33/336.12
(58) Field of Search ............. 128/200.24; 600/587–595; 606/130; 33/336.12

(56) References Cited

U.S. PATENT DOCUMENTS

| 4,960,118 A | * | 10/1990 | Pennock | ................ | 128/200.24 |
| 6,165,105 A | * | 12/2000 | Boutellier et al. | ............ | 482/13 |

FOREIGN PATENT DOCUMENTS

| JP | 55122110 | * | 9/1980 | .............. | 33/366.12 |
| JP | 58-159728 A | | 9/1983 | | |
| JP | 60-24410 A | | 2/1985 | | |
| JP | 5-200031 A | | 8/1993 | | |

* cited by examiner

*Primary Examiner*—Tony M. Argenbright
*Assistant Examiner*—Johnny H. Hoang
(74) *Attorney, Agent, or Firm*—Sidley Austin Brown & Wood LLP

(57) ABSTRACT

The rotational position sensor of the posture detection unit consists of a hollow housing including an insulating member and a movable body, the surface of which comprises a conductive member, such that the movable body can freely move in the housing. Contact points are located at the four corners of the side walls of the housing and essentially midway up the height of the side walls such that they protrude toward the central axis, and terminals that are individually electrically connected to these contact points are located on the surfaces of the side plates opposite from the surfaces that face each other, such that the terminals protrude outward. The distance between adjacent contact points is set to be slightly smaller than the diameter of the movable body, and the areas of the contact points that face the movable body are formed such that together they form a circle.

10 Claims, 13 Drawing Sheets

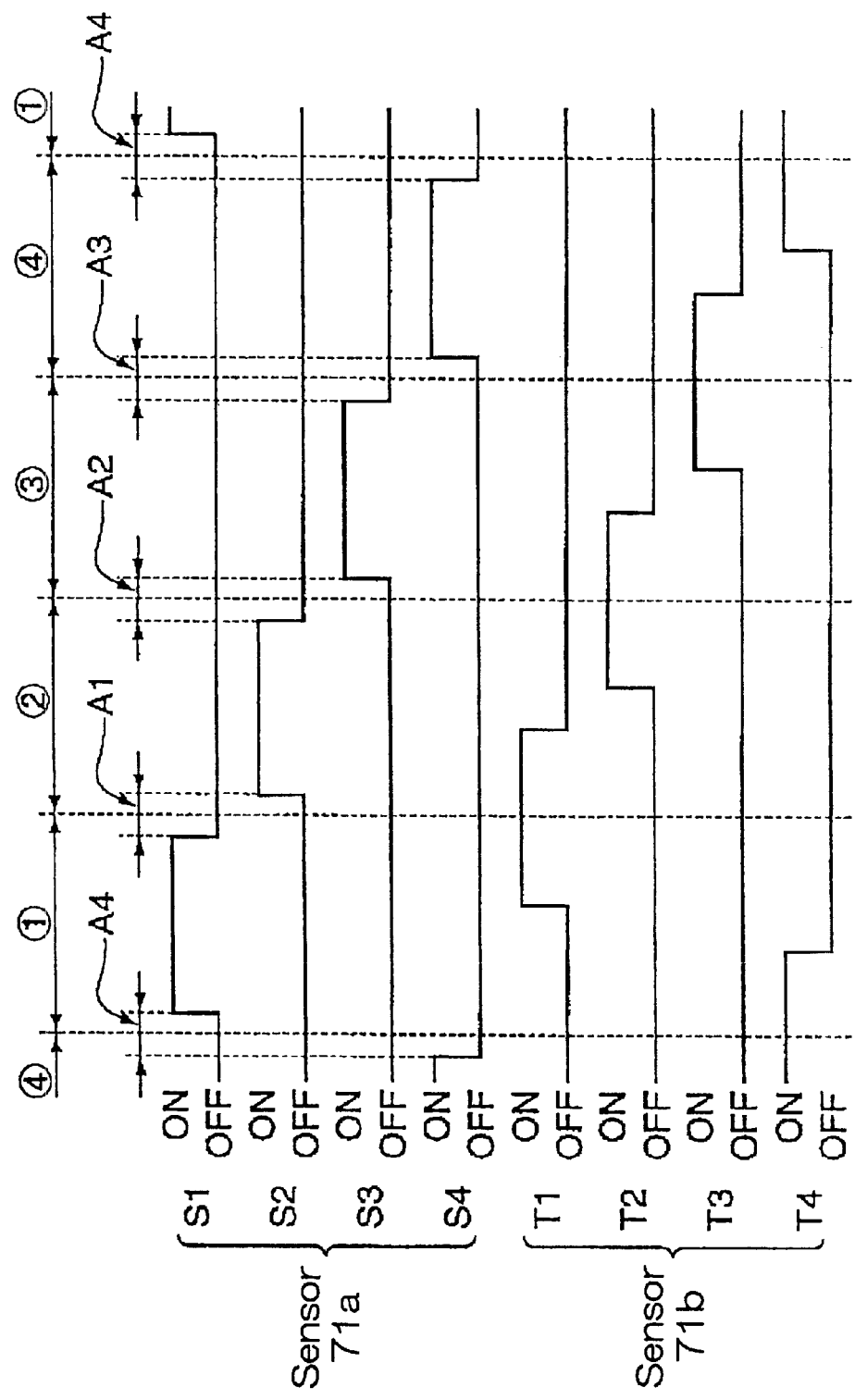

POSTURE DETECTING DEVICE AND BREATHING FUNCTION MEASURING DEVICE

This application is based on the application No. 2000-5882 filed in Japan, the content of which is hereby incorporated by reference.

BACKGROUND OF THE INVENTION

1. Field of the Invention

The present invention relates to a posture detecting device that detects the posture of the object of measurement, such as the position of the body of a test subject or the orientation of an object, as well as to a breathing function measuring device that includes this posture detecting device and that measures the breathing function of a test subject.

2. Description of the Related Art

A device having a movable body of which at least the surface comprises a conductive member, a container comprising an insulating member that houses the movable body such that it is contained and freely movable therein, and multiple contact points that are located at equal intervals around the central axis of the container and in the plane perpendicular to the central axis, and at least the surfaces of which comprise conductive members, wherein where the movable body moves, two adjacent points among the multiple contact points become short-circuited, is conventionally known as a posture detecting device that detects the posture of the object of measurement (Japanese Laid-open Patent Application Sho 58-159728, Japanese Laid-open Patent application Sho 60-24410).

A posture detecting device of this type is constructed such that hen it is fitted onto the object of measurement, i.e., a test subject, or example, the movable body moves and the two points that short-circuit change as the position of the body of the test subject changes, and therefore, the posture of the object of measurement may be detected by detecting whether each contact point is short-circuited.

However, using the conventional posture detecting device described above, the two contact points that are short-circuited change from one set of two contact points to another based on the movement of the movable body that occurs when the posture of the object of measurement changes. Therefore, between a state in which given two contact points are short-circuited and another state in which two other contact points are short-circuited, there is always a situation in which the movable body is in contact with only one contact point. This situation is termed a non-sensed state in this specification. This non-sensed state is a state in which no two contact points are short-circuited.

In addition, using the conventional posture detecting device described above, when the central axis of the container is essentially vertical due to the posture of the object of measurement, the movable body stays at a position at which it is separated from all contact points, and therefore, it is not in contact with any contact points. This state is termed an open state in this specification. This open state is also a state in which no two contact points are short-circuited, as in the case of a non-sensed state described above.

Therefore, when the position of the movable body, i.e., the posture of the object of measurement, is detected by detecting the short-circuited state of the contact points, where short-circuiting is not occurring between any contact points, it is not possible to determine whether the state is a non-sensed state in which the movable body is in contact with one contact point only, or an open state in which the movable body is in contact with none of the contact points.

Furthermore, it is generally known that when a person suffers from sleep apnea, in which a relatively long episode of non-breathing occurs frequently during sleep, the arterial blood oxygen level decreases significantly or arrhythmia results. In addition, non-breathing during sleep causes the sleep to be shallow, and may cause lethargy during the day. Testing for the sleep apnea described above has conventionally used polysomnography to measure the non-breathing state, such as the number of non-breathing episodes during sleep, as well as brain waves, eye movement and oxygen saturation. In this regard, a breathing function measuring device that is capable of easily measuring the non-breathing state of the sleeping test subject without the need for hospitalization has been proposed (Japanese Laid-open Patent Application Hei 5-200031).

Using the conventional breathing function measuring device described above, because it is necessary to seek the relationship between the breathing state and the posture of the test subject, a posture detecting device is fitted onto the test subject. When this is done, the burden on the test subject must be reduced by making it easy to fit the various detecting units onto the test subject.

An object of the present invention is to provide a posture detecting device that resolve the above problems, and that, based on a simple construction, is capable of reliably detecting the posture of the object of measurement.

Another object of the present invention is to provide a breathing function measuring device that includes the above posture detecting device and that reduces the burden on the test subject by making the fitting of the device to the test subject easy.

SUMMARY OF THE INVENTION

In order to attain these objects, the posture detecting device pertaining to the present invention comprises: a first movable body of which the surface comprise conductive member; a first container for housing the first movable body, such that it is contained and freely movable therein, and for having a first multiple contact points of which the surfaces comprise conductive members; a second movable body of which the surface comprise conductive member; and a second container for housing the second movable body, such that it is contained and freely movable therein, and for having a second multiple contact points of which the surfaces comprise conductive members, herein the first and second containers are positioned such that when the two adjacent contact points of the first container are not short-circuited by the first movable body, two adjacent contact points of the second container are short-circuited by the second movable body.

In order to attain the above objects, the breathing function measuring device pertaining to the present invention comprises: a wrapping member for wrapping around the chest or the abdomen of the object of measurement; a change amount detecting unit, which is located at one end of the wrapping member, for detecting the amount of change in the circumferential length of the chest or the abdomen due to the breathing effort of the object; and a posture detector, which is located inside the change amount detecting unit, for detecting the posture of the object.

BRIEF DESCRIPTION OF THE DRAWINGS

In the following description, like parts are designated by like reference numbers throughout the several drawings.

FIG. 6 comprises drawings showing the construction of a posture detection unit.

FIG. 8 is a drawing showing contact point short-circuited situations in regard to the rotational positions of rotational position sensors;

DETAILED DESCRIPTION OF THE PREFERRED EMBODIMENT

Figure 1:
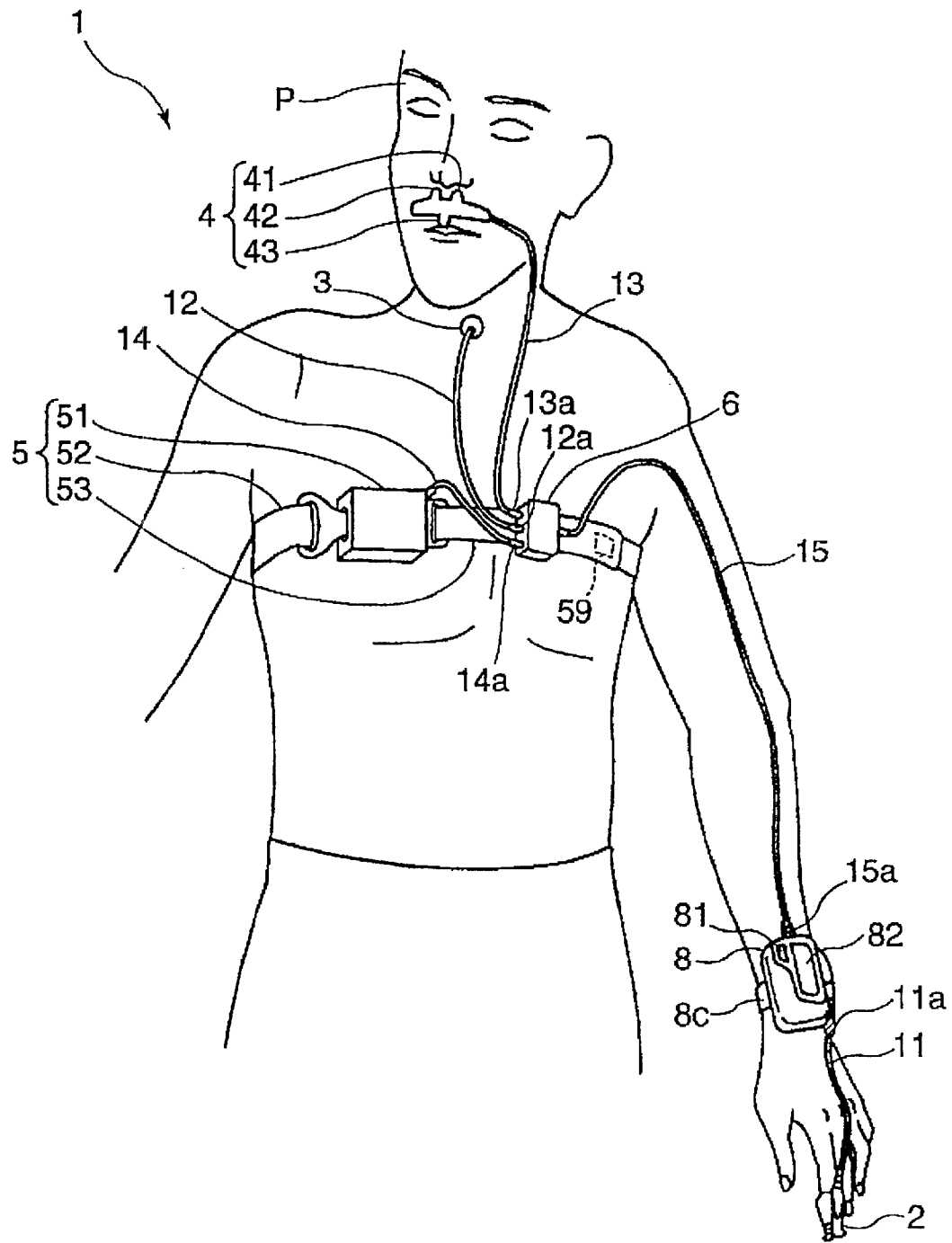
FIG. 1 is a drawing showing a situation in which a breathing function measuring device, one embodiment of the present invention, is fitted onto a test subject.

FIG. 1 is a drawing showing the situation in which one embodiment of the breathing function measuring device pertaining to the present invention is fitted onto a test subject.

This breathing function measuring device 1 is used to measure the breathing function of the test subject P, such as sleep apnea, and to indicate when a breathing abnormality is detected. The breathing function measuring device 1 includes an oxygen saturation detection unit 2, a sound detection unit 3, a breathing detection unit 4, a breathing effort detection unit 5, a relay unit 6, a posture detection unit 7 (FIG. 4) and a measurement processor 8.

The oxygen saturation detection unit 2 and the measurement processor 8 are connected via a connecting cable 11. The sound detection unit 3, breathing detection unit 4 and breathing effort detection unit 5 are connected to the relay unit 6 via connecting cables 12, 13 and 14, respectively. The relay unit 6 and the measurement processor 8 are connected via a relay cable 15 comprising a single cable into which the connecting cables 12, 13 and 14 are bound.

Plugs 11a through 14a are mounted to the tips of the connecting cables 11 through 14, and are detachably connected to the jack 8a (FIG. 10) of the measurement processor 8, and the jacks 6a, 6b and 6c (FIG. 10) of the relay unit 6, respectively. A plug 15a is mounted to the tip of the relay cable 15, and is detachably connected to the jack 8b (FIG. 10) of the measurement processor 8. The plugs 11a, 12a, 13a, 14a and 15a and the jacks 6a, 6b, 6c, 8a and 8b each comprise a connector, and serve as connecting means that enable a disconnectable electrical connection.

Figure 2:
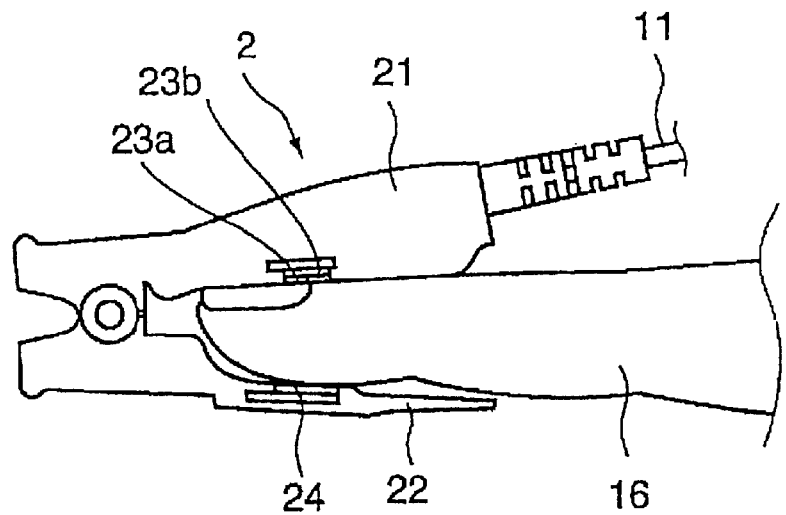
FIG. 2 is a drawing showing the construction of an oxygen saturation detection unit.

The construction of each component is explained below with reference to FIGS. 2 through 9. FIG. 2 is a drawing showing the construction of the oxygen saturation detection unit.

The oxygen saturation detection unit 2 detects the oxygen saturation of the arterial blood vessels in the fingertip. As shown in FIG. 2, clip plates 21 and 22, which are aligned such that the clip plate 21 is located on top of the clip plate 22, are connected via a shaft that supports one end of each clip plate, and the other ends of the clip plates are pressured toward each other via a spring (not shown in the drawings) so that the oxygen saturation detection unit 2 may be fitted onto the fingertip with the clip plates 21 and 22 sandwiching the finger 16 of the test subject. The top clip plate 21 includes an LED 23a that emits light of a wavelength having an absorption rate that depends on the blood oxygen level (red light, for example), and an LED 23b that emits light of a wavelength having an absorption rate that essentially does not depend on the blood oxygen level (infrared light, for example). A photodiode 24 that receives the light components from the light emitted from the LED 23a and 23b that has passed through the finger 16 is located at the position on the bottom clip plate 22 that corresponds to the LEDs 23a and 23b, so that photoreception signals corresponding to the intensity of the received light are transmitted to the measurement processor 8 via the connecting cable 11.

Returning to FIG. 1, the sound detection unit 3 is fitted near the throat of the test subject P using adhesive tape, for example. The sound detection unit 3 comprises a microphone that detects the sound in the trachea and the sound of snoring of the test subject P, and sound signals corresponding to the volume of the sound are transmitted to the measurement processor 8 via the connecting cable 12 and the relay cable 15.

Figure 3:
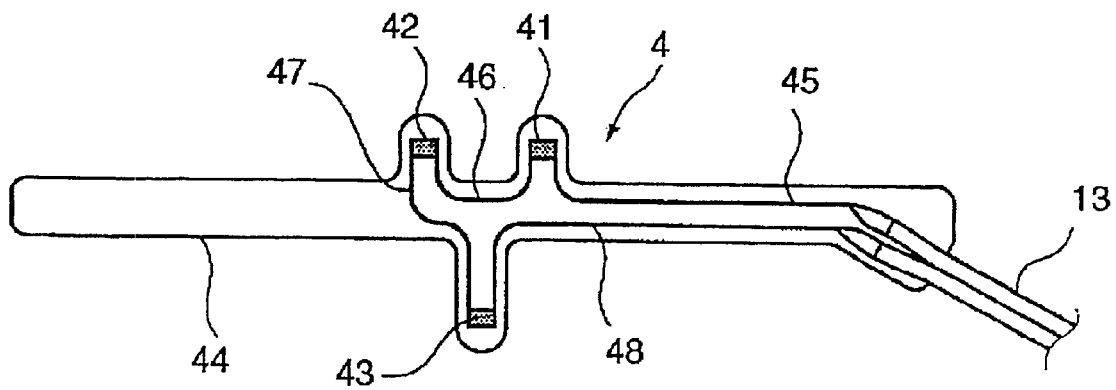
FIG. 3 is a drawing showing the construction of a breathing detection unit.

The breathing detection unit 4 detects the air flow generated by the breathing of the test subject P, and as shown in FIG. 3, comprises a left nostril breathing detection unit 41, a right nostril breathing detection unit 42 and a mouth breathing detection unit 43. The breathing detection unit 4 is applied under the nose of the test subject P using adhesive tape, for example, such that the left nostril breathing detection unit 41 and the right nostril breathing detection unit 42 face the entrance of each nostril and the mouth breathing detection unit 43 faces the mouth (see FIG. 1).

The left nostril breathing detection unit 41, the right nostril breathing detection unit 42 and the mouth breathing detection unit 43 of this breathing detection unit 4 each comprise a thermistor, for example. As shown in FIG. 3, they are serially connected in the housing 44 via conductive lines 45, 46, 47 and 48, and the conductive lines 45 and 48 are bound together into one line as the connecting cable 13, while being mutually insulated from each other.

When air flow from the nose or mouth reaches the left nostril breathing detection unit 41, the right nostril breathing detection unit 42 or the mount breathing detection unit 43, the temperature of that detection unit increases, and this increase appears as a change in the amount of resistance between the conductive lines 45 and 48. Therefore, in the breathing detection unit 4, the change in the amount of resistance is detected as a change in the potential between the conductive lines 45 and 48.

The breathing effort detection unit 5 is fitted onto the chest or the abdomen of the test subject P, and detects the amount of the change in the circumferential length of the chest or the abdomen that is caused by the breathing effort of the test subject P. The breathing effort detection unit 5 includes inelastic belt members that are wrapped around the chest or the abdomen of the test subject P such that the ends of the belt members overlap, and detects the amount of the change in the length of the overlap of the above ends caused by the change in the circumferential length of the chest or the abdomen caused by the breathing effort of the test subject P. In addition, by using inelastic belt members, the change in the circumferential length appears directly as the amount of change in the area of overlap.

Figure 4:
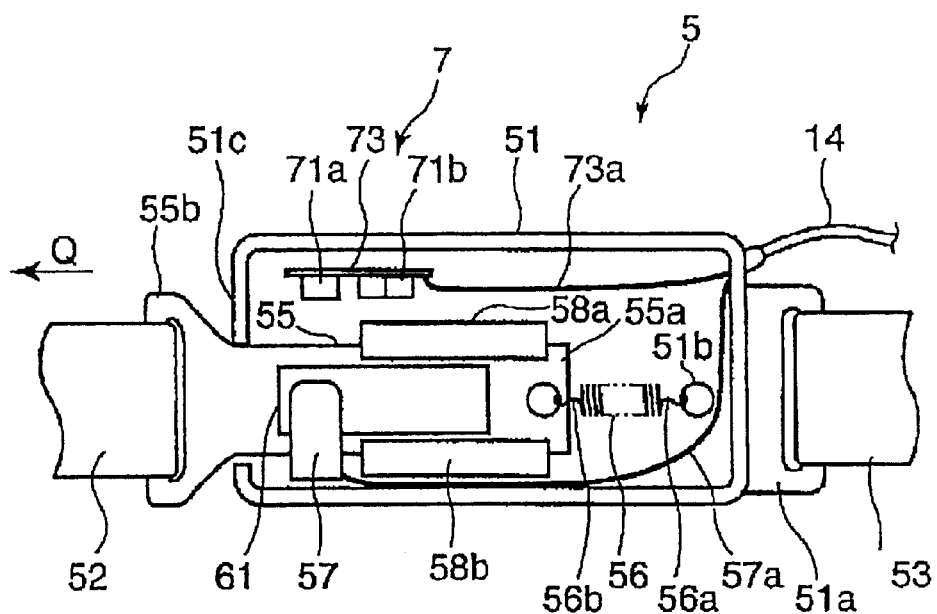
FIG. 4 is a drawing showing the internal construction of a detection box of a breathing effort detection unit.

FIG. 4 is a drawing showing the internal construction of the detection box of the breathing effort detection unit 5. The breathing effort detection unit 5 includes a detection box 51 and belts 52 and 53, and is fitted onto the chest of the test subject P in this embodiment, as shown in FIG. 1. As shown in FIG. 4, in the detection box 51 are located a moving plate 55, a spring 56, a photointerrupter 57, guide plates 58a and 58b, a posture detection unit 7 (described below), etc.

Inelastic belts are used for the belts 52 and 53 so that the change in the circumferential length of the chest may be accurately reflected in the shift of the moving plate 55 in the detection box 51. One end of the belt 52 is fixed to the left end 55b of the moving plate 55. The base 56a of the spring 56 is fixed to a prescribed area 51b of the detection box 51 while the tip 56b thereof is fixed to the right end 55a of the moving plate 55. One end of the belt 53 is fixed to the mounting area 51a located at the right end of the detection box 51.

The other ends of the belts 52 and 53 are fixed to each other via a surface fastener 59, as shown in FIG. 1, such that they may be removed and the mounting position thereof may be adjusted. By adjusting the lengths of the belts that wrap around the test subject P by adjusting the mounting position of the surface fastener 59, the breathing effort detection unit 5 may be placed close to the chest of the test subject P with an appropriate degree of elasticity of the spring 56.

Figure 5A:
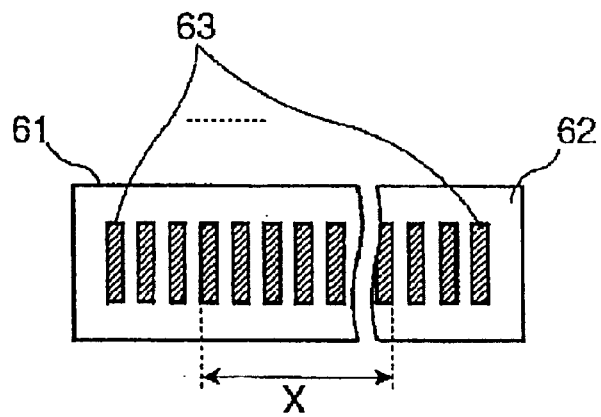
FIG. 5(a) is a front elevation of a calibration area.
Figure 5B:
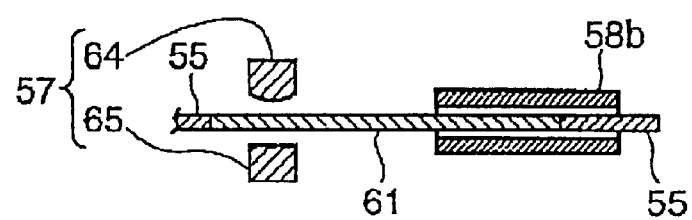
FIG. 5(b) is a cross-sectional view showing the positional relationships regarding the calibration area.

In FIG. 4, the moving plate 55 includes a calibration area 61. This calibration area 61 comprises a transparent film 62 on which a number of lines 63 having a prescribed width (0.03 mm in this embodiment, for example) are printed at equal intervals (0.06 mm in this embodiment, for example) along the length of the belt (the lateral direction in the drawing), as shown in FIG. 5(a). The photoemitter element (such as an LED) 64 and the photoreceptor element (such as a photodiode) 65 that comprise the photointerrupter 57 are located such that the calibration area 61 resides therebetween, as shown in FIG. 5(b).

In addition, in FIG. 4, the guide plates 58a and 58b are fixed to the detection box 51, and define the direction in which the moving plate 55 moves when the belt 52 is pulled in the direction of the arrow Q. Although only the guide plate 58b is shown in FIG. 5(b), each guide plate is formed such that the cross-section thereof has a C-shaped configuration and holds the moving plate 55 at the top and bottom thereof.

The spring 56 comprises an elastic member. The belts 52 and 53, the moving plate 55 and the detection box 51 comprise an inelastic belt member. The lines 63 comprise areas that have prescribed 13 characteristics. The photointerrupter 57 comprises a reader. The lines 63 also comprise shielding areas, and the area of the film 62 located between each line 63 comprises a light-permeable area.

As shown in FIG. 1, in this embodiment, the breathing effort detection unit 5 is fitted onto the chest of the test subject P, but it may be fitted onto the abdomen instead. In addition, a different elastic member, such as a rubber member, may be used in place of the spring 56.

As shown in FIG. 4, in this embodiment the calibration area 61 is located on the moving plate 55 and the photointerrupter 57 is fixed to the detection box 51. However, the present invention is not limited to this implementation, and the calibration area 61 may instead be located on the detection box 51 and the photointerrupter 57 may be mounted to the moving plate 55. In other words, it is acceptable if the amount of shift of the right end 55a of the moving plate 55 that comprises one end of the belt member relative to the left end 51c of the detection box 51 that comprises the other end of the belt member can be detected.

Returning to FIG. 1, the box-shaped relay unit 6 prevents the three connecting cables that connect the sound detection unit 3, the breathing detection unit 4 and the breathing effort detection unit to the measurement processor 8 from becoming tangled and crowded, and is fixed to the belt 53. The jacks 6a, 6b and 6c (FIG. 10) to which are mounted the plugs 12a, 13a and 14a at the tips of the connecting cables 12, 13 and 14 that connect the sound detection unit 3, the breathing detection unit 4 and the breathing effort detection unit 5, respectively, are located on one side surface of the relay unit 6. The relay cable 15 that connects to the measurement processor 8 is fixed to the opposite side surface thereof. In the relay unit 6, the three connecting cables 12, 13 and 14 are bound together such that the signals of each cable may be output via the single relay cable 15 while being insulated from each other.

The posture detection unit 7 detects the posture of the test subject P (i.e., whether the test subject P is standing, lying on his back, right side, left side or face down, etc.).

This posture detection unit 7 has rotational position sensors each comprising a conductive movable body closed off in a container having multiple contact points. Each movable body may move freely, and can enter a short-circuited state in which it short-circuits two adjacent contact points. When the movable body moves because the posture of the test subject P changes, it short-circuits different two contact points. The movable body has a non-sensed state in which it does not short-circuit any two contact points while it moves between one short-circuited state and another short-circuited state. This non-sensed state essentially occurs because there is a situation in which the movable body is in contact with only one contact point when it moves from one short-circuited state to another short-circuited state. However, the above non-sensed state cannot be distinguished from the open state, in which the movable body is not in contact with any contact points.

Therefore, the posture detection unit 7 of this embodiment has two of said rotational position sensors, and is fitted onto the test subject P such that the rotational position sensors are positioned relative to each other such that the rotational position sensors do not enter a non-sensed state at the same time.

Figure 6A:
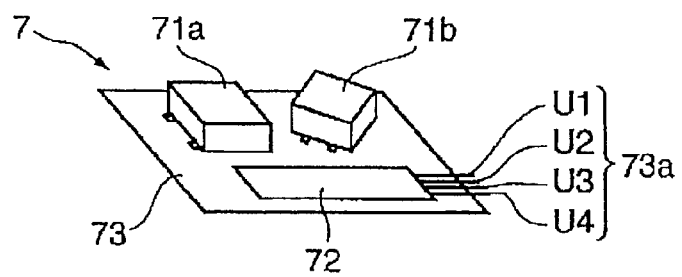
FIG. 6(a) is an external perspective view.
Figure 6B:
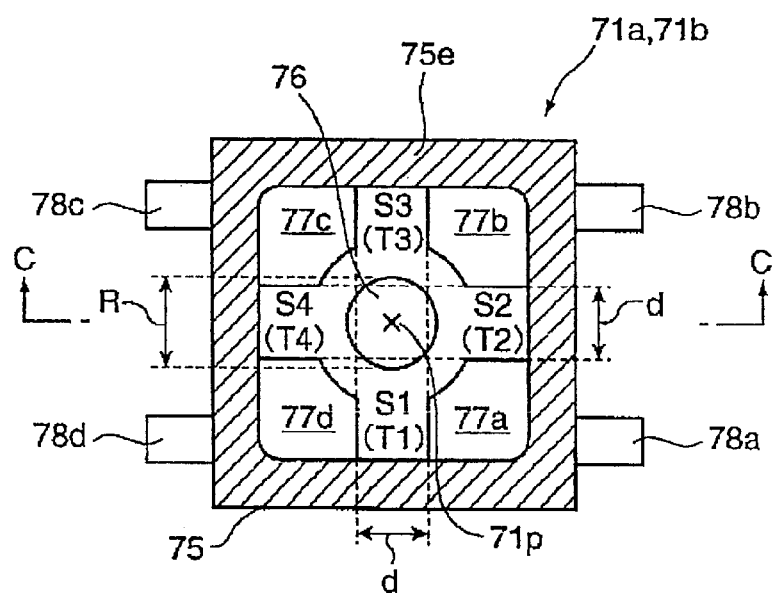
FIG. 6(b) is a transverse cross-sectional view of a rotational position sensor.
Figure 6C:
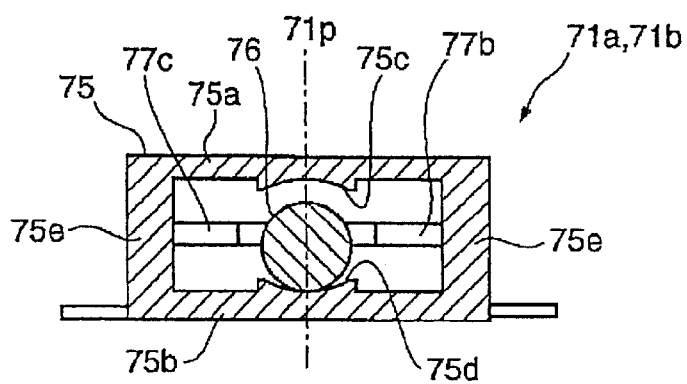
FIG. 6(c) is a C—C cross-sectional view of FIG. 6(b)
Figure 7A:
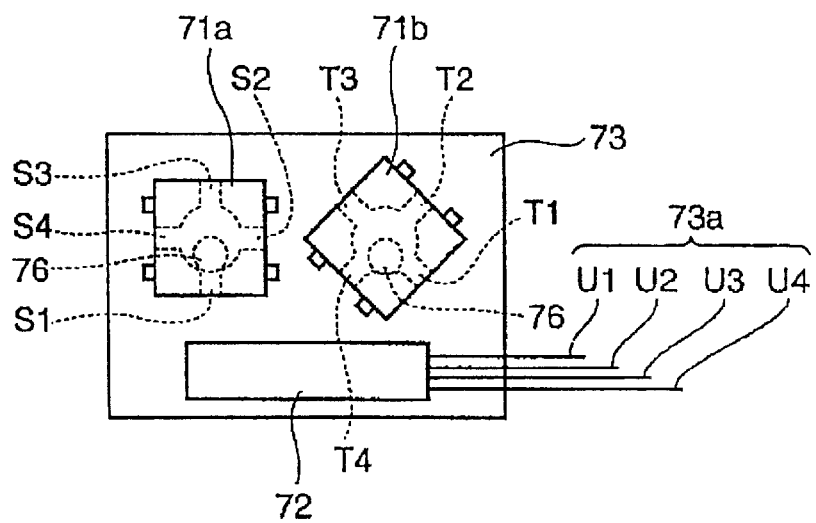
FIGS. 7(a) and 7(b) are drawings showing the positioning of the posture detection unit when the test subject is lying on his back.
Figure 7B:
Figure 9:
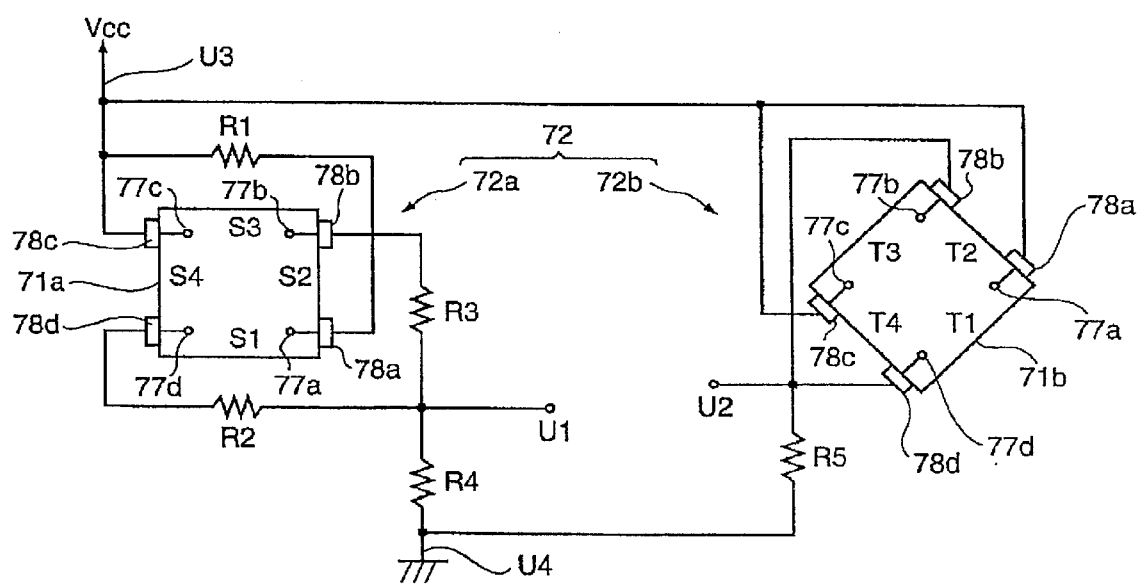
FIG. 9 is a circuit diagram showing a detection circuit of the posture detection unit.

FIG. 6 comprises drawings showing the construction of the posture detection unit. FIG. 6(a) is an external perspective view, FIG. 6(b) is a transverse cross-sectional view of the rotational position sensor, and FIG. 6(c) is a C—C cross-sectional view of FIG. 6(b). FIGS. 7(a) and 7(b) are drawings showing the positioning of the posture detection unit when the test subject is lying on his back. FIG. 8 is a drawing showing the contact points that are short-circuited based on the rotational positions of the rotational position sensors. FIG. 9 is a circuit diagram showing the detection circuit of the posture detection unit.

In FIG. 6(a), the posture detection unit 7 has rotational position sensors 71a and 71b, which have identical constructions, as well as a detection circuit 72, and are located on a circuit substrate 73. As shown in FIG. 4, the posture detection unit 7 is housed in the detection box 51 of the breathing effort detection unit 5. Because the posture detection unit 7 is housed in the detection box 51 in this way, it is not necessary to have a separate box to house the posture detection unit 7. This makes the fitting of the breathing function measuring device 1 easy, and can reduce the discomfort felt by the test subject P when the device is fitted onto him.

As shown in FIGS. 6(b) and 6(c), the rotational position sensors 71a and 71b each include a movable body 76, the surface of which comprises a conductive member, and a hollow housing (container) 75 comprising an insulating member. The movable body 76 is housed in the housing 75 such that it may freely move inside the housing. The housing 75 consists of a parallelepiped having a square top and bottom when viewed in a plan view, and having spherical concave areas 75c and 75d in the centers of the top plate 75a and the bottom plate 75b, respectively. In addition, contact points 77a, 77b, 77c and 77d, which comprise plate-shaped conductive members, are formed in the four corners of the side walls 75e and in approximately the midway points of the height of the walls 75e, such that they protrude toward the central axis 71p. Terminals 78a, 78b, 78c and 78d that are electrically connected to the contact points 77a, 77b, 77c and 77d, respectively, protrude outward from the opposite sides of the side wall 75e surfaces that face each other.

As shown in FIG. 6(b), the distance (d) from a contact point 77a, 77b, 77c or 77d and its adjacent contact point is set to be slightly shorter than the diameter R of the movable body 76. The areas of the contact points that face the movable body 76 are formed such that they are smooth and together comprise a circle having the central axis 71p as the center of the circle when seen from above. As shown in FIG. 6(a) and FIG. 7, the rotational position sensors 71a and 71b are placed on the circuit substrate 73 such that they are rotated around the central axis 7p (FIG. 6(b)) by a prescribed angle (45 degrees in this embodiment, for example) relative to each other (so that they have different phases). This circuit substrate 73 is fixed in the detection box 51 such that it faces downward, as shown in FIG. 4.

As shown in FIG. 6(b) and FIG. 7(a), the gap between the contact points 77a and 77d, the gap between the contact points 77a and 77b, the gap between the contact points 77b and 77c and the gap between the contact points 77c and 77d of the rotational position sensor 71a are termed contact areas S1, S2, S3 and S4, respectively. The gap between the contact points 77a and 77d, the gap between the contact points 77a and 77b, the gap between the contact points 77b and 77c and the gap between the contact points 77c and 77d of the rotational position sensor 71b are termed contact areas T1, T2, T3 and T4, respectively.

Using this construction, when the test subject P is standing, the movable body 76 sits in the concave area 75c, and therefore is not in contact with any of the contact points 77a, 77b, 77c or 77d, and all sets of two adjacent contact points are open (OFF).

In contrast, where the test subject P is lying on his back as shown in FIG. 7(b), the posture detection unit 7 is positioned such that the upper side of the sheet is the top (the ceiling side) and the lower side of the sheet is the bottom (the floor side) in FIG. 7(a). Therefore, the movable body 76 comes to sit between the contact points 77a and 77d in one of the rotational position sensors, i.e., the rotational position sensor 71a, and therefore, the contact points 77a and 77d comprising the contact area S1 become short-circuited (ON). The movable body 76 of the other rotational position sensor 71b comes to sit in the circular area at the tip of the contact point 77a, and therefore, a non-sensed state (OFF) is entered in which the connection between any two adjacent contact points is open.

The state of each contact area of the rotational position sensors 71a and 71b when the posture of the test subject changes will now be explained with reference to FIG. 8. As explained with reference to FIG. 7 above, when the test subject P is lying on his back, the movable body 76 sits between the contact points 77a and 77d in the rotational position sensor 71a, and the contact area S1 becomes short-circuited (ON). When the test subject P turns clockwise in the drawing from the state shown in FIG. 7, the movable body 76 comes to sit in the circular area at the tip of the contact point 77a, and a non-sensed state A1 is entered in which the connection between any two contact points is open (OFF). If the test subject turns once more, the movable body 76 of the rotational position sensor 71a comes to sit between the contact points 77a and 77b, and the contact area S2 becomes short-circuited (ON).

If the test subject continues to turns clockwise, the rotational position sensor 71a successively enters a non-sensed state A2 in which the movable body 76 sits in the tip area of the contact point 77b, a state in which the contact area S3 is ON, a non-sensed state A3 in which the movable body 76 sits in the tip area of the contact point 77c, a state in which the contact area S4 is ON, and a non-sensed state A4 in which the movable body 76 sits in the tip area of the contact point 77d. When the test subject returns to the position in which he is lying on his back, the contact area S1 becomes ON.

As described above, the range (1) corresponds to the state in which the test subject is lying on his back, the range (2) corresponds to the state in which he is on his left side, the range (3) corresponds to the state in which he is lying face down, and the range (4) corresponds to the state in which he is on his right side as in FIG. 8. The turning ON of the contact areas S1, S2, S3 and S4 corresponds to each posture, respectively. During the time in which the state of the rotational position sensor changes from a state in which one contact area is ON to a state in which another contact area is ON, a non-sensed state A1, A2, A3 or A4 exists in which none of the contact areas is ON. Therefore, if only this rotational position sensor 71a were used, a non-sensed state A1, A2, A3 or A4 and the open state that comes to exists when the test subject P is standing could not be distinguished from each other.

On the other hand, the rotational position sensor 71b is placed on the circuit substrate 73 such that it is rotated counterclockwise by a prescribed angle (45 degrees in this embodiment, for example) relative to the rotational position sensor 71a, as shown in FIG. 6(a) and FIG. 7(a). Therefore, if the test subject P turns clockwise in FIG. 7, the turning ON of the contact areas T1 through T4 is delayed by a ⅛ period relative to the turning ON of the contact areas S1 through S4, respectively, as shown in FIG. 8. Consequently, when the rotational position sensor 71a is in the non-sensed state A1, A2, A3 or A4, the contact area T1, T2, T3 or T4 becomes ON in the rotational position sensor 71b.

In this embodiment, the rotational position sensor 71b is placed on the circuit substrate 73 such that it is rotated counterclockwise by 45 degrees relative to the rotational position sensor 71a. However, the present invention is not limited to this implementation. It is acceptable if the rotational position sensors are placed such that one of the contact areas T1 through T4 becomes ON in the rotational position sensor 71b when the rotational position sensor 71a is in a non-sensed state A1, A2, A3 or A4, i.e., such that of the rotational position sensors 71a and 71b do not both enter a non-sensed state simultaneously. For example, the angle may be larger or smaller than 45 degrees, for example, or the rotational position sensor 71b may be placed such that it is rotated relative to the rotational position sensor 71a by −45 degrees or 135 degrees.

The detection circuit 72 connected to the rotational position sensors 71a and 71b will now be explained with reference to FIG. 9. In FIG. 9, the power supply voltage is $V_{CC}$, and the resistance values of the resistors R1 through R5 are $R_1$ through $R_5$.

The terminal 78a of the rotational position sensor 71a is connected to the power supply line U3 via the resistor R1. The terminal 78b is connected to the ground line U4 via a serial circuit comprising the resistors R3 and R4. The terminal 78c is directly connected to the power supply line U3. The terminal 78d is connected to the contact point between the resistors R3 and R4 via the resistor R2, and this contact point between the resistors R3 and R4 is connected to the output line U1. These connections comprise a first detection circuit 72a that outputs a voltage of a prescribed level to the output line U1.

At the same time, the terminals 78a and 78c of the rotational position sensor 71b are directly connected to the power supply line U3, respectively. The terminals 78b and 78d are directly connected to the output line U2, respectively, as well as to the ground line U4 via the resistor R5. These connections comprise a second detection circuit 72b that outputs a voltage of a prescribed level to the output line U2.

The connection cable 73a that extends from the circuit substrate 73 shown in FIG. 4 comprises the four conductive lines, i.e., output lines U1 and U2, the power supply line U3 and the ground line U4, each of which is insulated from the others.

Based on the circuit construction of the detection circuit 72 described above, the voltages V1 through V4 that are output to the output line U1 when the contact areas S1 through S4, respectively, of the rotational position sensor 71a are ON are as shown below.

$$V1 = V_{cc} \cdot R_4 / (R_1 + R_2 + R_4) \quad (1)$$

$$V2 = V_{cc} \cdot R_4 / (R_1 + R_3 + R_4) \quad (2)$$

$$V2 = V_{cc} \cdot R_4 / (R_3 + R_4) \quad (3)$$

$$V2 = V_{cc} \cdot R_4 / (R_2 + R_4) \quad (4)$$

The voltage V5 that is output to the output line U1 when all of the contact areas S1 through S4 are OFF is 0 (V5=0).

On the other hand, the voltage V6 that is output to the output line U2 when one of the contact areas T1 through T4 of the rotational position sensor 71b is ON is equal to voltage $V_{cc}$. The voltage V7 that is output to the output line U2 when all contact areas T1 through T4 of the rotational position sensor 71b are OFF is 0 (V7=0).

For example, when $V_{cc}$=5(V), $R_1$=100(kΩ), $R_2$=200(kΩ), $R_3$=51(kΩ), $R_4$=100(kΩ), and $R_5$=100(kΩ), the values V1=1.2(V), V2=2.0(V), V3=3.3(V), V4=1.7(V) and V6=5 (V) result.

By setting the resistance values of the resistors R1 through R4 of the first detection circuit 72a to appropriate values as shown above, voltages of difference levels may be output to the output line U1 when the contact areas S1 through S4 are ON, respectively. Based on this, it may be determined which of the contact areas S1 through S4 of the rotational position sensor 71a is ON, or whether all of the contact areas S1 through S4 are OFF. In addition, using the second detection circuit 72b, it may be determined whether one of the contact areas T1 through T4 of the rotational position sensor 71b is ON or whether all of the contact areas T1 through T4 are OFF.

Therefore, when only one rotational position sensor 71a is used, it cannot be determined when all of the contact areas S1 through S4 are OFF, whether the test subject is standing or he is lying down and the rotational position sensor is in a non-sensed state. By contrast, when the construction of this embodiment is used, even when all of the contact areas S1 through S4 of the rotational position sensor 71a are OFF, it can be determined that the test subject is lying down and that the rotational position sensor 71a is in a non-sensed state if one of the contact areas T1 through T4 of the rotational position sensor 71b is ON, and it can be determined that the test subject is standing if all of the contact points T1 through T4 are OFF.

Accordingly, it may be reliably determined whether the test subject is lying on his back, his left side or right side, or face down or standing.

In addition, by using the circuit construction shown in FIG. 9 for the detection circuit 72, determination may be made based on the four conductive lines U1 through U4, so that the number of signal lines from the posture detection unit 7 to the measurement processor 8 may be minimized. Further, because it suffices if the rotational position sensor 71b is used to determine whether any of the contact areas is ON or whether all of them are OFF, the second detection circuit 72b may have a simple circuit construction.

The second detection circuit 72b, however, may have the same circuit construction as the first detection circuit 72a. In this case, the contact area in the rotational position sensor 71b that is ON may be determined when the test subject is lying down and the rotational position sensor 71a is in a non-sensed state, and therefore, the postures between which the test subject is switching can be determined.

Returning to FIG. 1, the measurement processor 8 has a box shape and is fixed by wrapping a belt 8c that passes through the belt buckle (omitted in the drawing) on the rear side thereof around the wrist of the test subject P and fastening it using a surface fastener (omitted in the drawing). The measurement processor 8 also has a power switch 81 and a display unit 82 on its surface.

Figure 10:
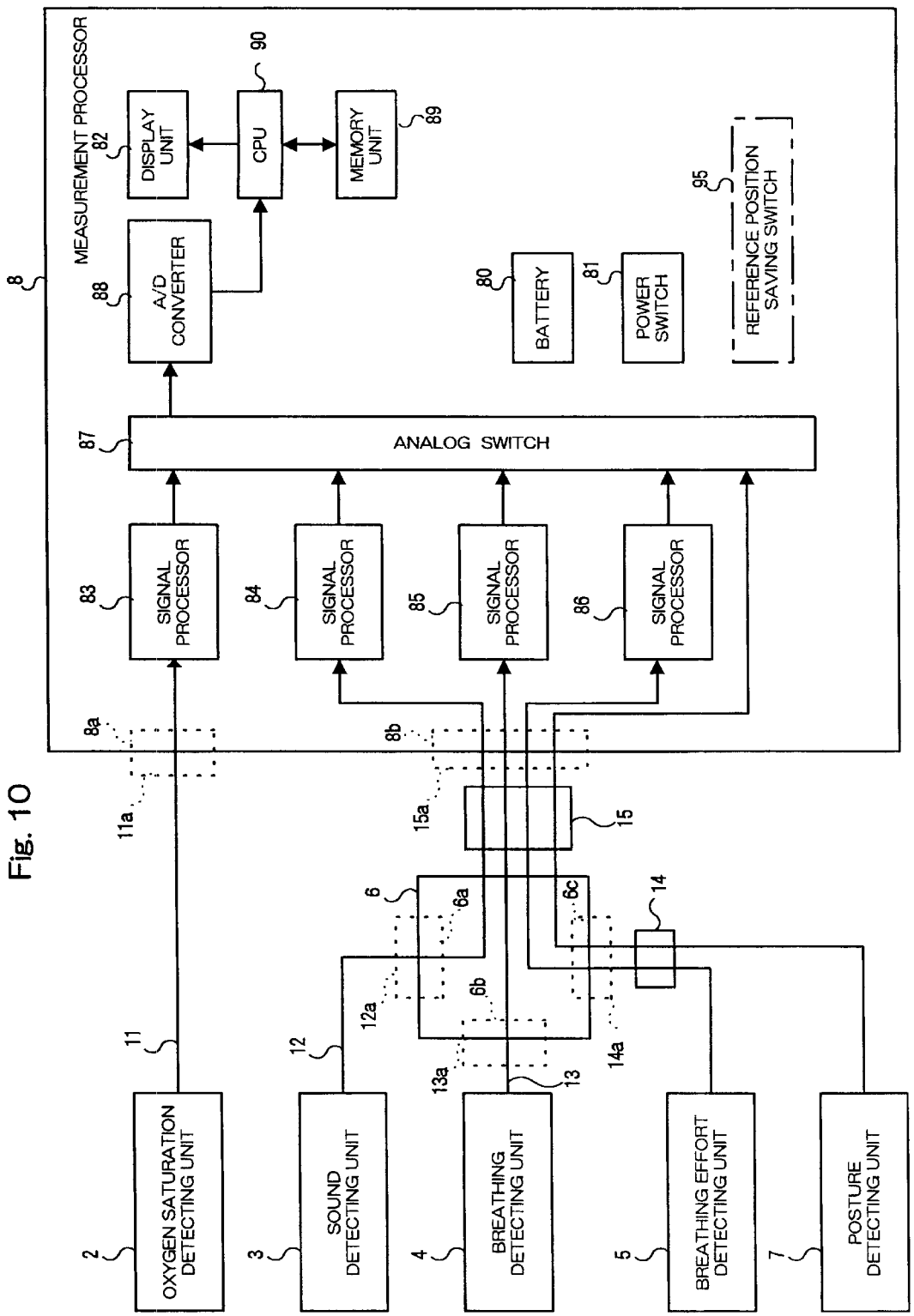
FIG. 10 is a block diagram showing the electrical construction of the breathing function measuring device.
Figure 11:
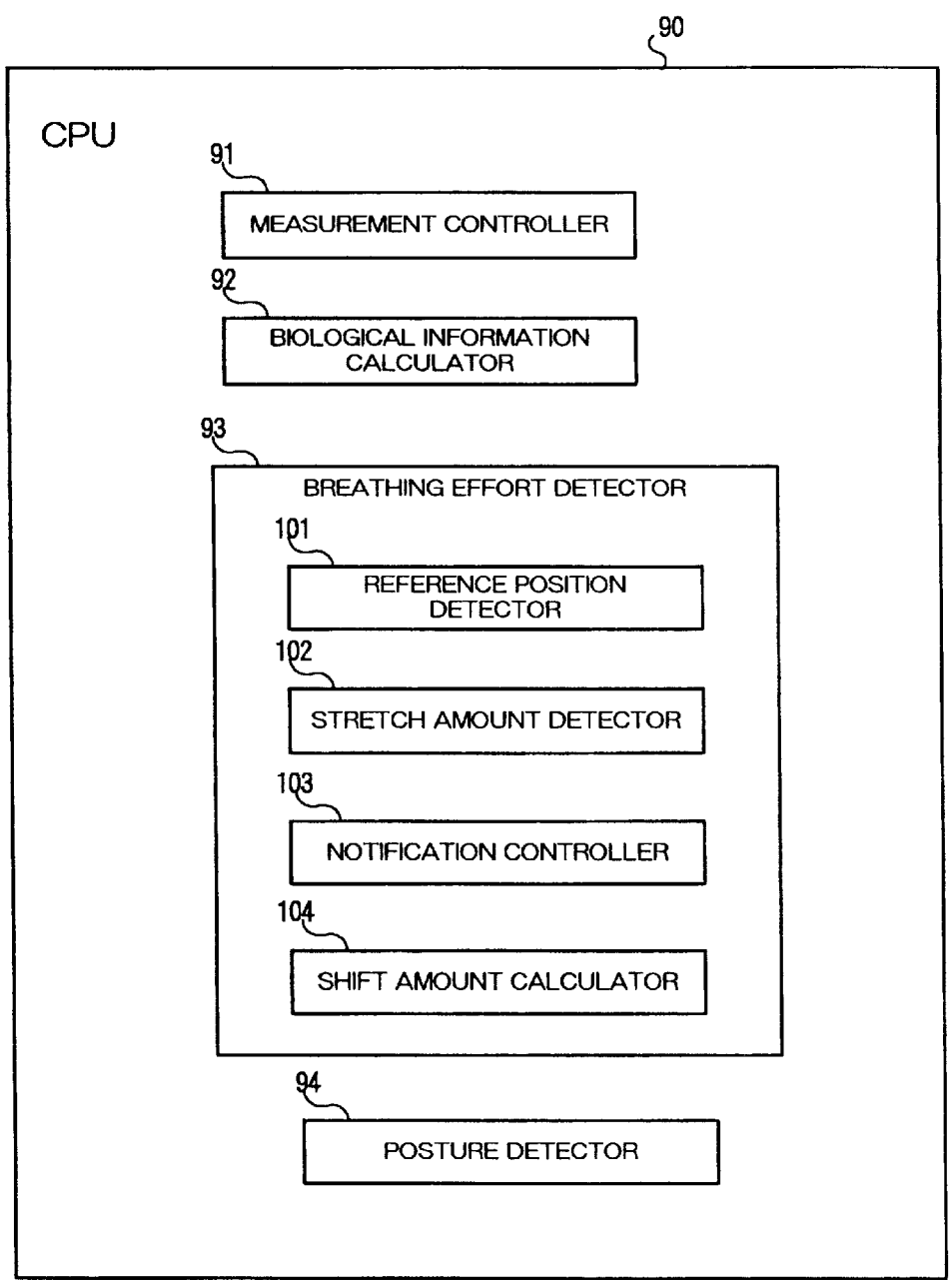
FIG. 11 is a block diagram showing the function blocks of a CPU.

The electrical construction of the measurement processor 8 will now be explained. FIG. 10 is a block diagram showing the electrical construction of the breathing function measuring device 1. FIG. 11 is a block diagram showing the function blocks of the CPU. Identical numbers are used for the members included in FIGS. 1 and 4.

The measurement processor 8 comprises a battery 80, a power switch 81, a display unit 82, signal processors 83 through 86, an analog switch 87, an A/D converter 88, a memory unit 89 and a CPU 90, as shown in FIG. 10.

The battery 80 comprises a 9V power supply, for example, and supplies operating power to each component. The power switch 81 begins power supply to each component from the battery 80. The display unit 82 comprises an LCD, etc., and displays the measurement results, etc.

The signal processors 83, 84, 85 and 86 receive photoreception signals from the photodiode 24 of the oxygen saturation detection unit 2, sound signals from the sound detection unit 3, detection signals corresponding to the resistance of the breathing detection unit 4, and photoreception signals from the photoreceptor element 65 of the photointerrupter 57 of the breathing effort detection unit 5, respectively, and perform amplification and waveform shaping of each signal.

Figure 12A:
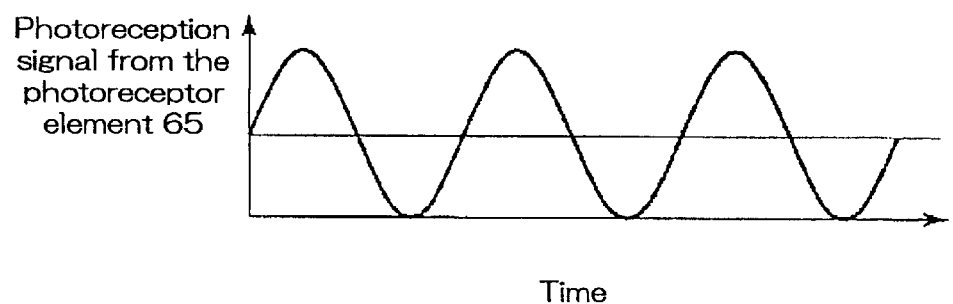
FIG. 12(a) is a drawing showing photoreception signals obtained from the photoreceptor element of a photointerrupter.

For example, where the circumferential length of the chest increases or decreases due to the breathing effort of the test subject and the calibration plate 61 moves between the photoemitter element 64 and the photoreceptor element 65 of the photointerrupter 57, the light emitted from the photoemitter element 64 is repeatedly transmitted and shielded. When this occurs, photoreception signals as shown in FIG. 12($a$) are obtained by the photoreceptor element 65, and after these signals are subjected to waveform shaping by the signal processor 86, the pulse signals as shown in FIG. 12($b$) are obtained.

The function of the signal processor 85 is to convert the change in the resistance into a change in voltage by impressing a preset voltage between the conductive lines 45 and 48 of the breathing detection unit 4.

The output signals from the signal processors 83 through 86 and the posture detection unit 7 are sequentially transmitted to the A/D converter 88 by the analog switch 87 controlled by the CPU 90, undergo A/D conversion, and are input to the CPU 90. The memory unit 89 comprises a ROM that stores the control program for the CPU 90 including preset fixed data, and a RAM or an EEPROM that temporarily stores the detection data. This RAM or EEPROM has the capacity to store detection data for 24 hours (three days of data, assuming that the test subject sleeps for eight hours), for example. The control program for the CPU 90 may be externally supplied via an IC card, etc. instead of being stored in the built-in ROM.

The CPU 90 includes as the function blocks thereof a measurement controller 91, a biological information calculator 92, a breathing effort detector 93 and a posture detector 94, as shown in FIG. 11.

Figure 13:
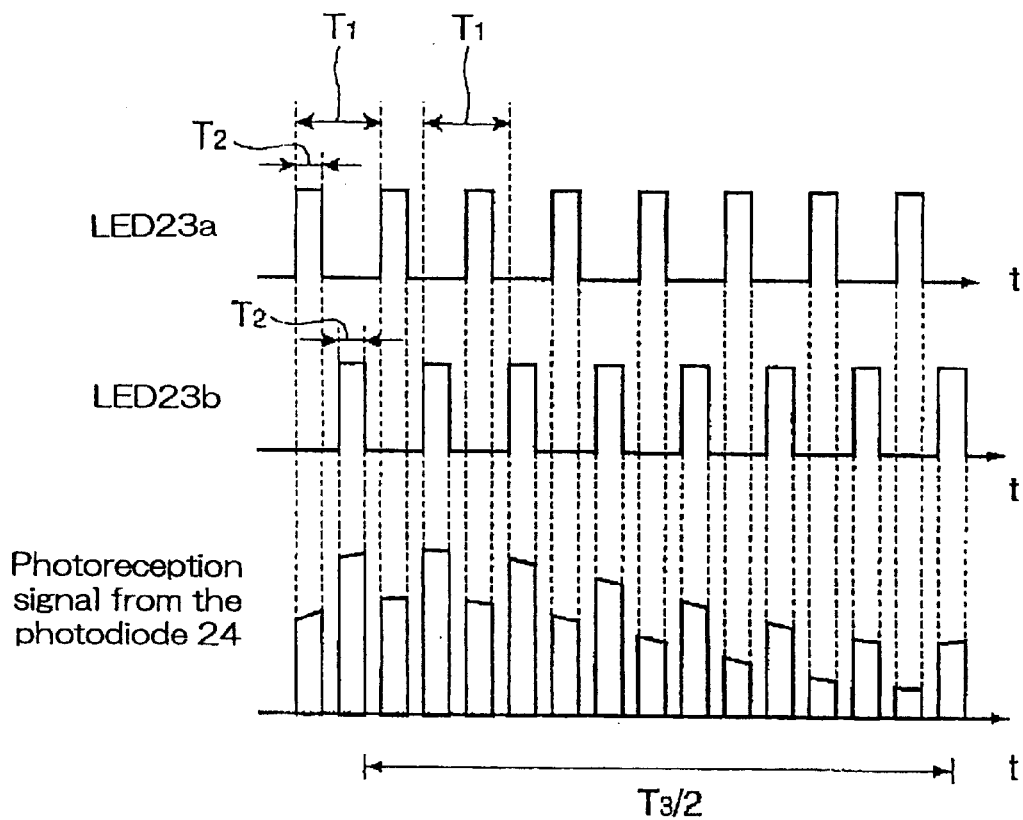
FIG. 13 is a drawing showing the photoemission from the LED of the oxygen saturation detection unit and the photoreception signals from the photodiode 24.

The measurement controller 91 controls the operation of each component and begins a measurement operation when the power switch 81 is turned ON. For example, as shown in FIG. 13, it causes the LEDs 23$a$ and 23$b$ of the oxygen saturation detection unit 2 to alternately emit light at prescribed intervals $T_1$ (10 msec, for example) for a prescribed period $T_2$ (2.5 msec, for example). The measurement controller 91 also causes the photoemitter element 64 of the breathing effort detection unit 5 to emit light.

The biological information calculator 92 performs the operations described in paragraphs (1) through (5) below, for example, to calculate various types of biological information at prescribed intervals (5 sec, for example) based on the signals obtained from each component, and stores the calculation results in the memory unit 89.

(1) Calculation of the heart beat rate based on the amplitude cycle $T_3$ ($T_3/2$ is shown in the drawing for convenience sake) of the photoreception signals from the photodiode 24 of the oxygen saturation detection unit 2, as shown in FIG. 13.

(2) Calculation of the oxygen saturation based on the level of each photoreception signal from the photodiode 24 when the LEDs 23$a$ and 23$b$ of the oxygen saturation detection unit 2 emit light, as shown in FIG. 13.

Figure 14:
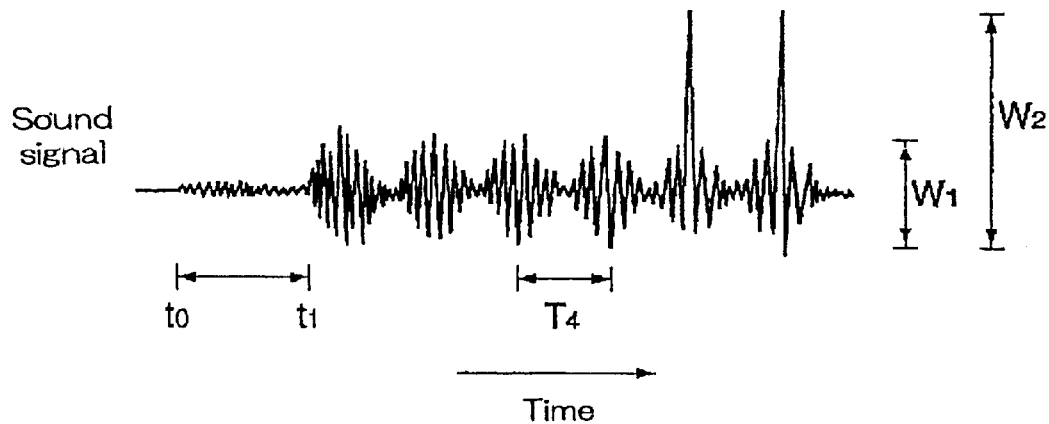
FIG. 14 is a drawing showing the sound signals from the sound detection unit.

(3) Comparison of the amplitude W of the sound signals from the sound detection unit 3 with a preset level, and determination regarding the breathing state, as shown in FIG. 14. For example, the biological information calculator 92 determines that the trachea sound does not exist due to non-breathing in the period from the time $t_0$ to the time $t_1$, as well as determines the amplitude $W_1$ to indicate normal breathing sounds, and the amplitude $W_2$ to indicate snoring sounds. In addition, it also calculates the rate of breathing per unit time and the length of the period over which non-breathing continued based on the peak-to-peak interval $T_4$.

Figure 15:
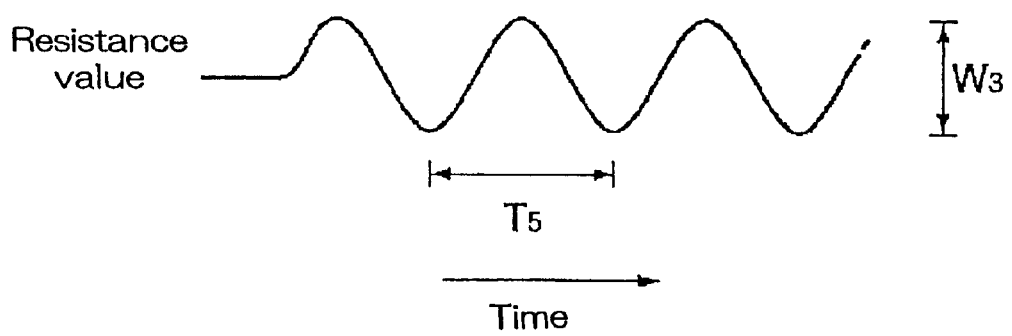
FIG. 15 is a drawing showing the changes in resistance in the breathing detection unit.

(4) Calculation of the rate of breathing per unit time and length of the period over which non-breathing continued based on the resistance change cycle $T_5$ in the breathing detection unit 4, as shown in FIG. 15. In addition, determination of the intensity of breathing based on the amplitude $W_3$ between peaks.

(5) Calculation of the number of non-breathing episodes per unit time and the number of non-breathing episodes per posture determined by the posture detector 94.

Returning to FIG. 11, the breathing effort detector 93 determines whether the test subject P is making a breathing effort based on the signals from the breathing effort detection unit 5. The breathing effort detector 93 includes as the function blocks thereof a reference position detector 101, a stretch amount detector 102, an notification controller 103 and a shift amount calculator 104.

The reference position detector 101 assumes the amount of stretch of the spring 56 when the power switch 81 is turned ON to be zero, and stores the position of the calibration plate 61 detected by the photointerrupter 57 in the memory unit 89 as the reference position.

The stretch amount detector 102 determines whether the amount of stretch of the spring 56 falls within a prescribed range when the breathing effort detection unit 5 is fitted to the test subject P. The stretch amount detector 102 performs this determination at prescribed intervals throughout the measurement.

The above prescribed range is the range within which the optimal tensile strength (elasticity) is attained (the detection range by the photointerrupter 57 is the range X shown in FIG. 5($a$), for example). This range is sought in advance based on the relationship of the tensile strength to the amount of stretch of the spring 56, and is saved in the memory unit 89.

This prescribed range may be defined by the length of the area in which the two ends of the belt member (the moving plate 55 and the detection box 51 in FIG. 4) overlap with each other. For example, it is a range defined by the length of the above overlap area when the detection position detected by the photointerrupter 57 is at the left edge of the range X shown in FIG. 5($a$), i.e., the upper limit, and the length of the above overlap area when the above detection position is at the right edge of the range X, i.e., the lower limit.

When the amount of stretch of the spring 56 falls within the above prescribed range, the notification controller 103 performs display to that effect in the display unit 82 and informs the test subject P. When the amount of stretch of the spring 56 is outside the prescribed range during measurement, the notification controller 103 performs display to that effect in the display unit 82 and informs the test subject P. The notification controller 103 also stores as data in the memory unit 89 the fact that the amount of stretch is outside the prescribed range, together with the measurement data and the data on the elapsed time. This data is expressed by setting a predesignated bit to 1, for example. In other words, if the predesignated bit is 0, it is indicated that the measurement took place within the prescribed range.

Figure 12B:
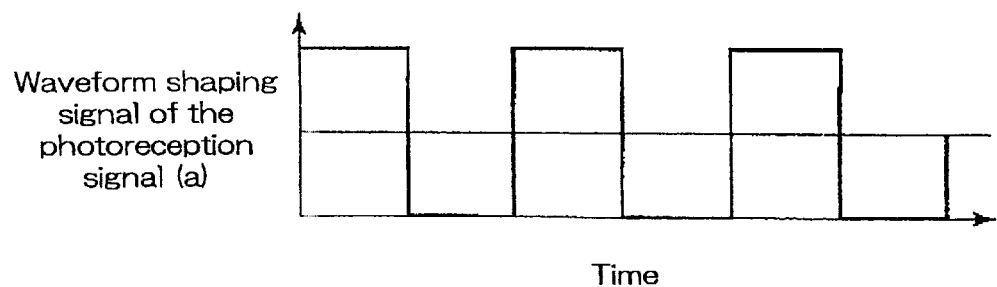
FIG. 12(b) is a drawing showing the photoreception signals shown in FIG. 12(a) that have undergone waveform shaping by a signal processor.

The shift amount calculator 104 calculates the amount of change in the chest size (the circumferential length of the chest) of the test subject due to the breathing effort based on the number of photoreception signal pulses from the photoreceptor element 65 of the photointerrupter 57, as shown in FIG. 12(b). The shift amount calculator 104 seeks the intensity of the breathing effort and the number of times the breathing effort was stopped (the number of ten-second or longer periods during which the breathing effort stopped, for example) and stores this data in the memory unit 89.

The posture detector 94 determines the posture of the test subject P based on the voltage levels in the output lines U1 and U2 (FIG. 9) of the posture detection unit 7. In other words, where the voltage V output to the output line U1 is in accordance with the equation (1) above, i.e., V=V1, the posture detector 94 determines that the test subject is lying on his back. Where the voltage V output to the output line U1 is in accordance with the equation (2) above, i.e., V=V2, the posture detector 94 determines that the test subject is lying on his left side. Where the voltage V is in accordance with the equation (3), i.e., V=V3, the posture detector 94 determines that the test subject is lying on his face. Where the voltage V is in accordance with the equation (4) above, i.e., V=V4, the posture detector 94 determines that the test subject is lying on his right side. Where the voltage V output to the output line U1 is 0 (V=0), and the voltage output to the output line U2 is $V_{cc}(V=V_{cc})$ the test subject P is determined to be lying down. Where the voltages V output to the output lines U1 and U2 are both 0 (V=0), the test subject P is determined to be standing.

As described above, an inelastic belt member comprising a detection box 51, belts 52 and 53 and a moving plate 55 is fitted onto the test subject P, and a spring 56 (an elastic means) is located between either end of the belt member, such that the belt member is pulled to be tightened. Furthermore, a calibration area 61 on a moving plate 55 that moves as the circumferential length of the chest or abdomen increases or decreases due to the breathing effort of the test subject P is detected by a photointerrupter 57 to seek the amount of movement. Using this construction, the change in the above circumferential length is directly sought, and the amount of change in the circumferential length may be accurately obtained. Therefore, it may be accurately determined whether or not the test subject is breathing, and a patient who should be diagnosed as suffering from sleep apnea will not be overlooked.

Further, display is performed in a display unit 82 to the effect that the amount of stretch of the spring 56 falls within the above prescribed range. Using this construction, when the breathing effort detection unit 5 is fitted onto the test subject P, the position at which the surface fastener 59 is fixed should be adjusted when adjusting the length of the belts 52 and 53 so that the display unit 82 indicates that the stretch amount is within the prescribed amount. As a result, the breathing effort detection unit 5 may be easily fitted such that the belt member has an appropriate tensile strength. Therefore, if the tensile strength when the breathing effort detection unit 5 is fitted is insufficient, the belts become too loose and do not fit snugly onto the test subject, making it difficult to accurately detect the amount of change in the circumferential length of the chest or the abdomen, but this problem may be resolved, and the amount of change in the circumferential length of the chest or the abdomen due to the breathing effort may be accurately detected.

In addition, where the amount of stretch of the spring 56 during measurement exceeds the above prescribed range, data indicating this fact is stored in a memory unit 89. As a result, it may be determined through post-measurement analysis whether or not reliable and accurate measurement was carried out.

It is also acceptable if the device includes a reference position saving switch 95, as shown by the dashed chain dot line in FIG. 10, so that the amount of stretch of the spring 56 when this reference position saving switch 95 is turned ON is deemed zero, and the position of the calibration area 61 at that time may be stored in the memory unit 89 as a reference position.

The movable body 76 is not limited to a conductive sphere as described in the above embodiment. The movable body 76 may comprise a movable conductive member, and may comprise a conductive liquid such as mercury, for example.

In the above embodiment, the posture detection unit 7 is housed in the detection box 51 of the breathing effort detection unit 5, but the present invention is not limited to this implementation. The posture detection unit 7 may instead be housed in the relay unit 6. When this construction is used, a separate box to house the posture detection unit 7 is not needed as in the case of the above embodiment. Consequently, the fitting of the breathing function measuring device 1 onto the test subject may be easily performed, and the discomfort felt by the test subject P due to the fitting of the breathing function measuring device 1 may be reduced.

Figure 16:
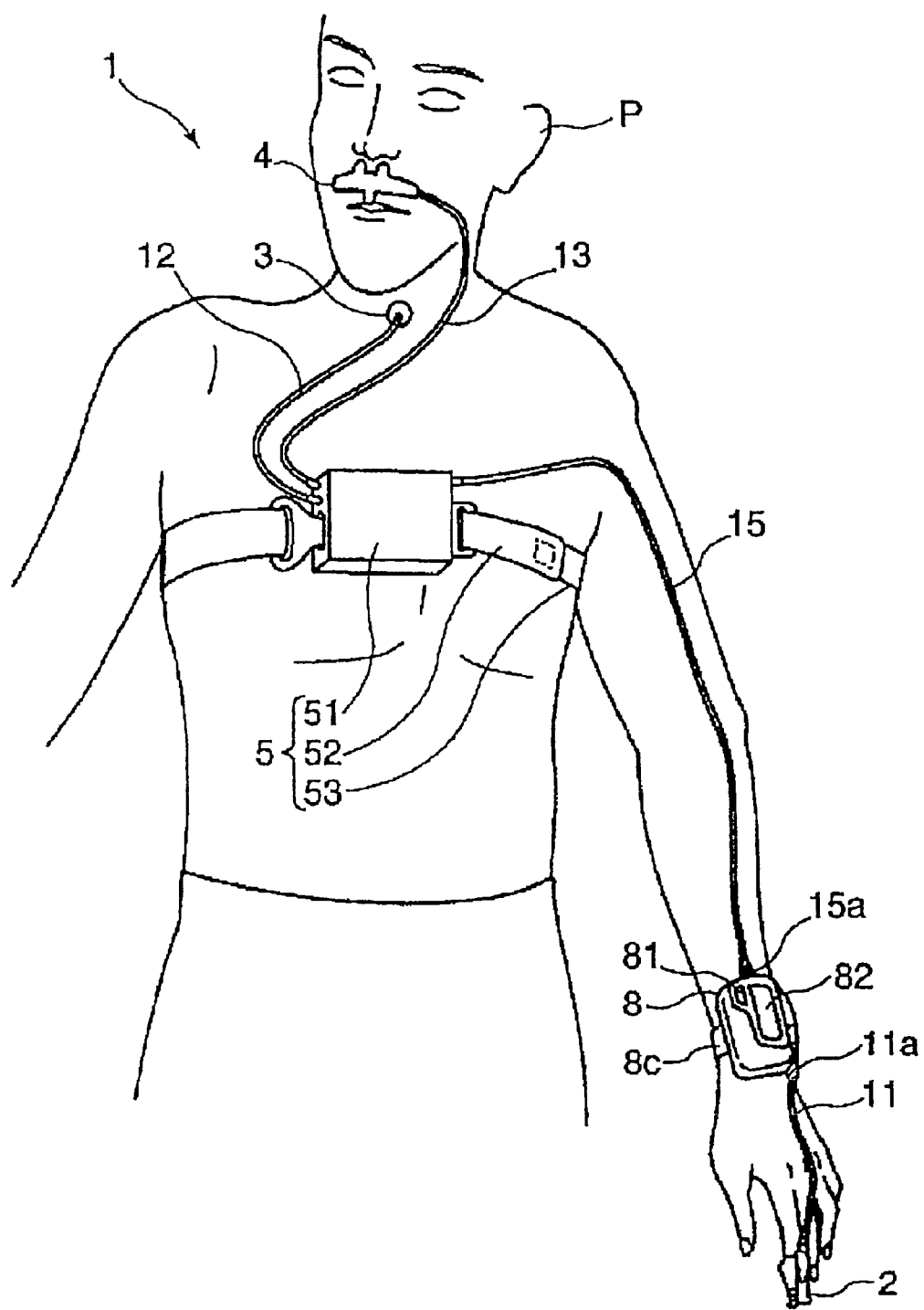
FIG. 16 is a drawing showing a configuration in which the relay unit is housed in the detection box of the breathing effort detection unit.

As shown in FIG. 16, the relay unit 6 may also be housed in the detection box 51 of the breathing effort detection unit 5. In this case, a separate box for the relay unit 6 is no longer needed, the fitting of the breathing function measuring device 1 onto the test subject may be more easily performed, and the discomfort felt by the test subject P due to the fitting of the breathing function measuring device 1 may be further reduced.

As explained above, using the present invention, multiple movable bodies enter a short-circuited state in which they each short-circuit two adjacent contact points when they are placed between two adjacent contact points out of multiple contact points, and when the movable bodies move due to a change in the posture of the object of measurement, a non-sensed state in which no two contact points are short-circuited is entered when the movable bodies are between one short-circuited state and another short-circuited state. Due to the construction in which the central axes of the multiple containers are essentially parallel to each other and a non-sensed state does not occur simultaneously in the multiple movable bodies, the posture of the object of measurement may be reliably detected.

Furthermore, using the present invention, the multiple containers and the multiple contact points are formed such that all containers and all of the multiple contact points have the identical constructions, respectively. The multiple containers are fitted onto the object of measurement such that they are rotated by a prescribed degree around the central axes relative to each other so that the positions of the multiple contact points around the central axes have different phases. Using this construction, a simple and low-cost construction may be realized in which the central axes of multiple containers are essentially parallel to each other, and in which a non-sensed state does not occur in the multiple movable bodies simultaneously.

Using the present invention, when the first movable body among the multiple movable bodies is in a short-circuited state, a detection signal is output by which the two adjacent contact points that are short-circuited may be determined, as well as a detection signal by which it may at least be determined whether the second movable body among the multiple movable bodies is in a short-circuited or non-sensed state. Using this construction, the posture of the object of measurement may be reliably detected. Because a detection signal is output by which it may be determined whether the second movable body is in a short-circuited or a non-sensed state may be detected, it may be determined through a simple construction whether a short-circuited state or a non-sensed state is present.

Moreover, using the present invention, because the posture detecting means is located in the change amount detection unit, fewer items need to be fitted onto the test subject compared to the situation in which the posture detecting means is housed in a separate housing, and consequently, the burden on the test subject may be reduced.

Although the present invention has been fully described by way of examples with reference to the accompanying drawings, it is to be noted that various change and modifications will be apparent to those skilled in the art. Therefore, unless otherwise such changes and modifications depart from the scope of the present invention, they should be construed as being including therein.

What is claimed is:

1. A posture detecting device comprising:
   a first movable body having a surface comprising a plurality of conductive members;
   a first container for housing the first movable body, such that said first movable body is contained and freely movable therein, and for having a first plurality of contact points, said first container having surfaces comprising conductive members;
   a second movable body having a surface comprising a plurality of conductive members; and
   a second container for housing the second movable body, such that said second movable body is contained and freely movable therein, and for having a second plurality of contact points, said second container having surfaces comprising conductive members,
   wherein the first and second containers are positioned such that when two adjacent contact points of the first plurality of contact points of the first container are not short-circuited by the first movable body, two adjacent contact points of the second plurality of contact points of the second container are short-circuited by the second movable body.

2. A posture detecting device according to claim 1, wherein
   each of said first plurality of contact points is located at equal intervals around a central axis of the first container and in a plane perpendicular to the central axis of the first container, and
   wherein each of said second plurality of contact points is located at equal intervals around a central axis of the second container and in a plane perpendicular to the central axis of the second container.

3. A posture detecting device according to claim 1, wherein said first and second containers are fitted onto an object of measurement such that a phase of a position of the second plurality of contact points is different from a phase of a position of the first plurality of contact points.

4. A posture detecting device according to claim 1, wherein a central axis of the first container and a central axis of the second container are approximately parallel to each other.

5. A posture detecting device according to claim 1, wherein when two adjacent contact points are not short-circuited, said movable body exists between one pair of adjacent contact points and another pair of adjacent contact points.

6. A posture detecting device according to claim 1, wherein said first and second containers have an identical construction.

7. A posture detecting device according to claim 1, wherein said posture detecting device detects at least that an object of measurement is lying down.

8. A posture detecting device according to claim 1, further comprising a first circuit, when two adjacent contact points of the first container are short-circuited by the first movable body, said first circuit for outputting a signal to discriminate the short-circuited two adjacent contact points, and a second circuit for outputting a signal to discriminate whether two adjacent contact points of the second container are short-circuited.

9. A breathing function measuring device comprising:
   a wrapping member for wrapping circumferentially around a portion of an object of measurement;
   a change amount detecting unit, which is located at one end of the wrapping member, for detecting an amount of change in the circumferential length of the portion of the object due to the breathing effort of the object; and
   a posture detector, which is located inside the change amount detecting unit, for detecting a posture of the object at said portion.

10. A breathing function measuring device according to claim 9, wherein said posture detector comprises:
   a first movable body having a surface which comprises a plurality of conductive members;
   a first container for housing the first movable body, such that said first movable body is contained and freely movable therein, and for having a first plurality of contact points, said first container having surfaces comprising conductive members;
   a second movable body having a surface comprising a plurality of conductive members; and
   a second container for housing the second movable body, such that said second movable body is contained and freely movable therein, and for having a second plurality of contact points, said second container having surfaces comprising conductive members,
   wherein the first and second containers are positioned such that when two adjacent contact points of the first plurality of contact points of the first container are not short-circuited by the first movable body, two adjacent contact points of the second plurality of contact points of the second container are short-circuited by the second movable body.

* * * * *

UNITED STATES PATENT AND TRADEMARK OFFICE
CERTIFICATE OF CORRECTION

PATENT NO. : 6,514,218 B2
DATED : February 4, 2003
INVENTOR(S) : Shinji Yamamoto It is certified that error appears in the above-identified patent and that said Letters Patent is hereby corrected as shown below:

<u>Title page,</u>
Item [57], ABSTRACT,
Line 3, delete "comprises", and insert -- includes --.

<u>Column 7,</u>
Line 49, delete "7p", and insert -- 71p --.

<u>Column 9,</u>
Line 25, delete "$V_{cc}$", and insert -- $V_{cc}$, --.
Line 61, delete "$V2 = V_{cc} \cdot R_4/(R_3 + R_4)$", and insert -- $V3 = V_{cc} \cdot R_4/(R_3 + R_4)$ --.
Line 61, delete "$V2 = V_{cc} \cdot R_4/(R_2 + R_4)$", and insert -- $V4 = V_{cc} \cdot R_4/(R_2 + R_4)$ --.

Signed and Sealed this

Twenty-fourth Day of February, 2004

JON W. DUDAS
*Acting Director of the United States Patent and Trademark Office*